(12) United States Patent
Blacklaw

(10) Patent No.: US 7,357,021 B2
(45) Date of Patent: Apr. 15, 2008

(54) METHODS OF MONITORING DOWNHOLE CONDITIONS

(75) Inventor: David William Blacklaw, Katy, TX (US)

(73) Assignee: Welldynamics, Inc., Spring, TX (US)

( * ) Notice: Subject to any disclaimer, the term of this patent is extended or adjusted under 35 U.S.C. 154(b) by 217 days.

(21) Appl. No.: 11/101,100

(22) Filed: Apr. 7, 2005

(65) Prior Publication Data
US 2005/0224229 A1 Oct. 13, 2005

(30) Foreign Application Priority Data
Apr. 8, 2004 (GB) ................................. 0407982.8

(51) Int. Cl.
*E21B 47/10* (2006.01)
(52) U.S. Cl. .................. 73/152.31; 73/152.32
(58) Field of Classification Search ............ 73/152.18, 73/152.32, 861.18, 861.27, 861.28, 861.29
See application file for complete search history.

(56) References Cited

U.S. PATENT DOCUMENTS

| | | | |
|---|---|---|---|
| 4,046,220 A | 9/1977 | Glenn, Jr. | |
| 4,208,906 A | 6/1980 | Roberts, Jr. | |
| 4,715,747 A | 12/1987 | Behrens | |
| 5,392,645 A * | 2/1995 | Kleppe | 73/195 |
| 5,561,245 A * | 10/1996 | Georgi et al. | 73/152.02 |
| 5,892,860 A | 4/1999 | Maron et al. | |
| 6,109,595 A | 8/2000 | Lecours | |
| RE37,283 E | 7/2001 | Kluth et al. | |
| 6,268,911 B1 | 7/2001 | Tubel et al. | |
| 6,354,147 B1 * | 3/2002 | Gysling et al. | 73/61.79 |
| 6,369,881 B1 | 4/2002 | Wang | |
| 6,532,839 B1 | 3/2003 | Kluth et al. | |
| 6,556,630 B1 | 4/2003 | Brinsfield et al. | |
| 6,618,677 B1 * | 9/2003 | Brown | 702/13 |
| 6,813,962 B2 * | 11/2004 | Gysling et al. | 73/861.26 |
| 6,874,361 B1 * | 4/2005 | Meltz et al. | 73/152.32 |
| 6,931,945 B2 * | 8/2005 | Takeda et al. | 73/861.25 |
| 7,009,707 B2 * | 3/2006 | Beresford et al. | 356/478 |
| 7,139,667 B2 * | 11/2006 | Rothman et al. | 702/50 |
| 7,168,311 B2 * | 1/2007 | Zisk et al. | 73/152.31 |

(Continued)

FOREIGN PATENT DOCUMENTS

EP 1484473 A 8/2004

(Continued)

OTHER PUBLICATIONS

"Downhole monitoring—Listening with light" published in Apr. 2003 Offshore Engineering magazine on p. 26-30.

(Continued)

*Primary Examiner*—Hezron Williams
*Assistant Examiner*—John Fitzgerald
(74) *Attorney, Agent, or Firm*—Smith IP Services, P.C.

(57) ABSTRACT

Methods of monitoring various downhole conditions are described, including a system for determining and/or identifying the flow of fluid in a well, determining sand production in a well, identifying localized events in a well, determining the apparent flow velocity of fluid flowing through a downhole conduit, and/or monitoring the strain in downhole tubulars. These determinations may be made by monitoring signals received from one or more sensors located in a well and analysing the signals, such as their frequency and timing.

3 Claims, 7 Drawing Sheets

U.S. PATENT DOCUMENTS

| | | | |
|---|---|---|---|
| 7,224,872 B2 * | 5/2007 | Goldner et al. | 385/104 |
| 2002/0174728 A1 | 11/2002 | Beresford et al. | |
| 2002/0194932 A1 | 12/2002 | Gysling et al. | |
| 2006/0214098 A1 * | 9/2006 | Ramos | 250/256 |

FOREIGN PATENT DOCUMENTS

| | | |
|---|---|---|
| EP | 1484473 | 12/2004 |
| GB | 1473991 A | 1/1975 |
| GB | 1473991 | 5/1977 |
| GB | 2151414 A | 7/1985 |
| GB | 2171218 A | 8/1986 |
| GB | 2312995 A | 11/1997 |
| GB | 2363852 | 1/2002 |
| GB | 2397885 A | 4/2004 |
| GB | 2396011 | 6/2004 |
| GB | 2397885 | 8/2004 |
| GB | 2396011 A | 9/2004 |
| GB | 2399637 | 9/2004 |
| GB | 2382136 | 10/2004 |
| WO | 93/09404 | 5/1993 |
| WO | 93/14382 | 7/1993 |
| WO | 94/20825 | 9/1994 |

OTHER PUBLICATIONS

Downhole monitoring—Glamour models age reliably published in Sep. 2002 Offshore Engineer magazine on pp. 17-19.

Three pages discussing Fiber Bragg Gratings from an unknown book—publication date unknown, but was certainly before priority date.

Examination Report for UK application No. GB0507066.9 dated Mar. 16, 2007.

UK Search Report issued for GB Patent Application No. 0713435.6 dated Sep. 7, 2007 (6 pages).

* cited by examiner

METHODS OF MONITORING DOWNHOLE CONDITIONS

FIELD OF THE INVENTION

The present invention relates to methods of monitoring downhole conditions in oil and/or gas wells and arrangements of apparatus therefor and more particularly but not exclusively relates to the use of fiber optic or electronic monitoring methods for oil and/or gas wells.

BACKGROUND OF THE INVENTION

Conventionally, it is known to conduct "noise log" operations in oil/gas wells. The noise log tool is an instrument sensitive to acoustic signals and is run into a well on the end of an electrical cable attached to, or contained within a wireline, in order to move it past zones of interest.

Accordingly, as the noise log tool is drawn past the zones of interest, anomalies or differences from a baseline log (i.e. a log already conducted) can be used to infer information on the flow of the production fluids (i.e. the oil and/or gas) passing up the well from the production zones. Such conventional noise log technology, however, provides only a "one-shot" survey, in that it only provides information when the noise log tool is actually run into the well and therefore cannot provide a permanent monitoring system since the noise log tool cannot reside permanently within the well. Furthermore, the measurements provided by the noise log tool may be affected by the very presence of the noise tool in the flow.

It is also known to use optical fibers deployed in oil and/or gas wells, where the optical fibers are provided with a number of Fiber Bragg Gratings (FBGs). By way of background, FBGs have been in use for many years in the telecommunication industry and have been used more recently in the downhole oil and gas industry. Hitherto, the FBGs have been used to act as sensors to monitor seismic activity in the oil and/or gas reservoir; in other words, they listen for movement such as cracking in the rock of the reservoir. An article entitled "Downhole Monitoring: Listening with Light" published in April 2003 on pages 26 to 30 in Offshore Engineer publication discusses such known use of FBGs.

SUMMARY OF THE INVENTION

According to a first aspect of the present invention there is provided a method of determining and/or identifying the flow of fluid in a well comprising monitoring the signal received from two or more sensors located in a well and analysing the frequency of said signals over time to determine a flow regime for production of fluids.

Preferably, the method further comprises continued monitoring of the signal received from the one or more sensors to create an acoustic profile of the well.

Typically, the sensors are provided on an elongate member and preferably, the sensors comprise optically based sensors and the elongate member comprises an optical fiber. Most preferably, the sensors comprise Fiber Bragg Gratings (FBGs).

Typically, the signal that is monitored is an interferometric signal of a section of the elongate member located between two sensors. Preferably, a plurality of interferometric signals are monitored for a respective plurality of sections of the elongate member.

The method preferably further comprises creating a flow regime based upon the signals monitored and preferably further comprises comparing the flow regime to a reference flow regime.

According to a second aspect of the present invention there is provided a method of determining sand production in a well comprising monitoring the signal received from one or more sensors located in a well and analysing the frequency of said signals for indications of sand production.

Typically, the sensors are one or more optical based sensors which are typically provided on an optical fiber.

Preferably the one or more sensors are Fiber Bragg Gratings and preferably there are a plurality of FBGs provided on the optical fiber, and more preferably, said FBGs are arranged to be vertically spaced apart when deployed in the well.

Preferably, the frequency of said signals is analyzed by comparing the signals from two vertically spaced apart sensors.

According to a third aspect of the present invention there is provided a method of identifying localized events in a well comprising monitoring the signal received from one or more sensors located in a well and analyzing the frequency of said signals for localized events.

Typically, such localized events can include any one, more than one or all of the following:
 fluid flow behind a casing or liner string located in the well;
 flow occurring due to leaks in production tubing;
 flow occurring due to cross-flow between production zones of the well.

Typically, the method according to the third aspect is used in conjunction with, or following, the method according to the first aspect of the present invention, where the localised events are identified by comparing the signal received from one sensor with the signals received from one or more of the other sensors located in the well.

The method of the third aspect may be conducted whilst the well is shut in; in other words, the method of the third aspect may be conducted whilst the well has been prevented from producing production fluids.

According to a fourth aspect, the present invention provides a method of determining the apparent flow velocity of fluid flowing through a conduit, comprising the steps of:
 monitoring the signal received from a first sensor and noting the time at which an event is sensed by the first sensor;
 monitoring the signal received from a second sensor and noting the time at which the event is sensed by the second sensor; and
 calculating the velocity of fluid flowing in the conduit using the difference in time noted at the first and second sensors.

Typically, the conduit is a downhole tubing and is preferably a production tubing for carrying oil and/or gas from a production zone of hydrocarbon reservoir to the surface of the well. Typically, the distance between the first and second sensors is known.

The event may be a thermal event such as a change in temperature in the production fluid and may be a naturally occurring thermal event such as a change in the temperature of the production fluid leaving the production zone of the reservoir.

Alternatively, the thermal event may be an induced thermal event caused by fluid being injected into the production tubing at a different temperature to the temperature of the production fluid.

Alternatively, the event may be an acoustic event and further may be an induced acoustic event such as a sound created by a collision of a moveable member such as a piston.

Alternatively, the event may be a pressure event such as an increased pressure of the production fluid which may be generated by injection of fluid into the production tubing; in this situation, the first and second sensors are preferably first and second pressure sensors.

According to a fifth aspect, the present invention provides a method of monitoring the strain in downhole tubulars comprising the steps of:

measuring the time of travel of a signal from a signal transmitter to a signal receiver through the wall of the downhole tubular; and calculating the distance travelled by the signal from the signal transmitter to a signal receiver through the wall of the downhole tubular.

Preferably, the method firstly comprises the steps of providing the tubular with at least one receiver and may further comprise providing the tubular with a transmitter. Typically, the transmitter and receiver are respectively an acoustic transmitter and receiver.

Typically, the downhole tubular comprises a casing or liner string and the receiver is typically located on the outer surface of the casing or liner string on a cable protection means at a casing joint coupling means.

BRIEF DESCRIPTION OF THE DRAWINGS

Embodiments of the present invention will now be described, by way of example only, with reference to the accompanying drawings, in which.

DESCRIPTION OF PREFERRED EMBODIMENTS

Figure 7:
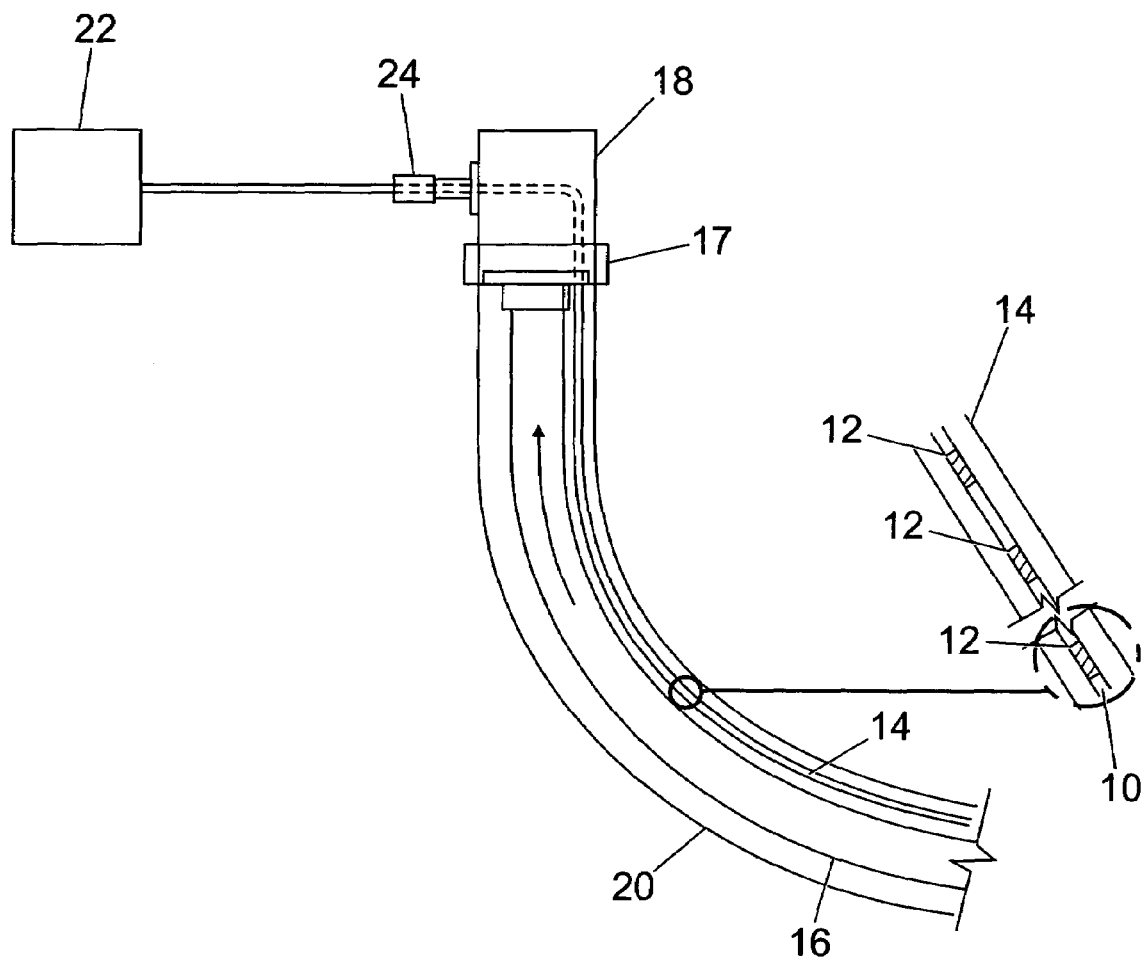
FIG. 7 is a schematic diagram of an optical fiber comprising a plurality of FBGs deployed within a protective tube downhole within an oil/gas well.

An optical fiber 10 provided with a plurality of FBGs 12 is installed downhole in an oil/gas/water well of interest as shown in FIG. 7 by any suitable conventional technique, one example of which is that disclosed in U.S. Pat. No. 6,532,839. The FBGs 12 are written onto a section of the optical fiber by one of the known techniques, for example, by Ultra-violet light writing. The locations of such FBGs 12 can be as close as 15 mm from one another and the maximum number of FBGs that can be multiplexed and interrogated on a single fiber varies with the manufacturer of the instrumentation, but is typically in the region of 30 to 100 FBGs 12 per fiber.

The FBGs 12 are placed in appropriate and desired locations within the well depending upon the particular deployment mechanism chosen, and it should be noted that the optical fiber 10 carrying the FBGs 12 can be deployed with, or instead of, conventional electronic or fiber downhole monitoring systems in a similar fashion thereto; that is the optical fiber 10 carrying the FBGs 12 can be fixed inside or deployed into a protective tube 14 attached to one of the downhole tubular strings such as the production tubing string 16 which acts as a conduit for the flow of the produced hydrocarbons from the production zone reservoir to the surface. As shown in FIG. 7, the production tubing is hung from a tubing hanger 17 located within a wellhead 18 located at the surface of the well within a casing string 20 as is known in the art.

As is known, the deployed FBGs 12 respond to strain or other displacement of the optical fiber 10, such as temperature, and the response can be measured by monitoring data analysis equipment 22 which is coupled to the upper end of the optical fiber 10 (see FIG. 7). The upper end of the optical fiber 10 and protective tube 14 exit the casing string 20 through the wellhead 18 out through a sealed wellhead outlet 24.

It should be noted that interferometric techniques, which have hitherto been used to monitor seismic movement, can be also used to make measurements of the acoustic signal sensed in the fiber section between two FBGs 12.

The reader should note that while the embodiments of the methods described below will be useful in their own right, many of the embodiments can be additionally useful through use of a conventional temperature profile in conjunction to the measured acoustic profile. In other words, the FBGs 12 can be used in their conventional manner to act as multiple single point temperature measurement sensors, in conjunction with the acoustic embodiments described subsequently. This may be additionally useful because temperature profiles are conventionally used to obtain information on the performance of a well and additional acoustic information or analysis (or simply confirmation of existing interpretation) can be achieved if the additional acoustic information in accordance with the present invention is utilised.

Embodiment 1

Determination and Identification of Flow Regime from an Acoustic Profile

One or more embodiments in accordance with the first aspect of the present invention will now be described.

When a fiber 10 containing FBGs 12 as described above is deployed downhole, an interferometer can be used to measure the acoustic signal between each successive FBG 12. If, for example, a sensor system comprising 20 FBGs 12 are present on a deployed fiber 10, separate acoustic measurements can be made of the 19 sections between these FBGs 12. For any given period of time, an "acoustic profile" can therefore be created for the section of the well across which the FBGs 12 are deployed.

This is of interest because aspects of the acoustic signal such as the frequency components and their amplitude, will be a function of parameters such as the fluid type and flow regime of the flow past the sensor system. For given types of fluids, flow regimes and flow patterns can be characterised in terms of the properties of the acoustic signal generated, and thus the flow regime past the sensor system can be identified by comparison to a series of reference flow regimes or flow patterns.

Embodiment 2

Sand Detection

One or more embodiments in accordance with the second aspect of the present invention will now be described.

Sand flowing with the production fluid will generate noise as it impinges upon any restriction or otherwise comes in contact with any solid object, such as the wall of the production tubing 16. In relation to the production of clean fluids, sand-contaminated fluids generate discernible high-frequency components of the flow noise.

When an FBG 12 sensor system is deployed as described above, spectral analysis of the acquired acoustic signal can be used, particularly when referenced to an initial 'baseline' data set, to identify sand production or flow past the sensor.

Figure 1:
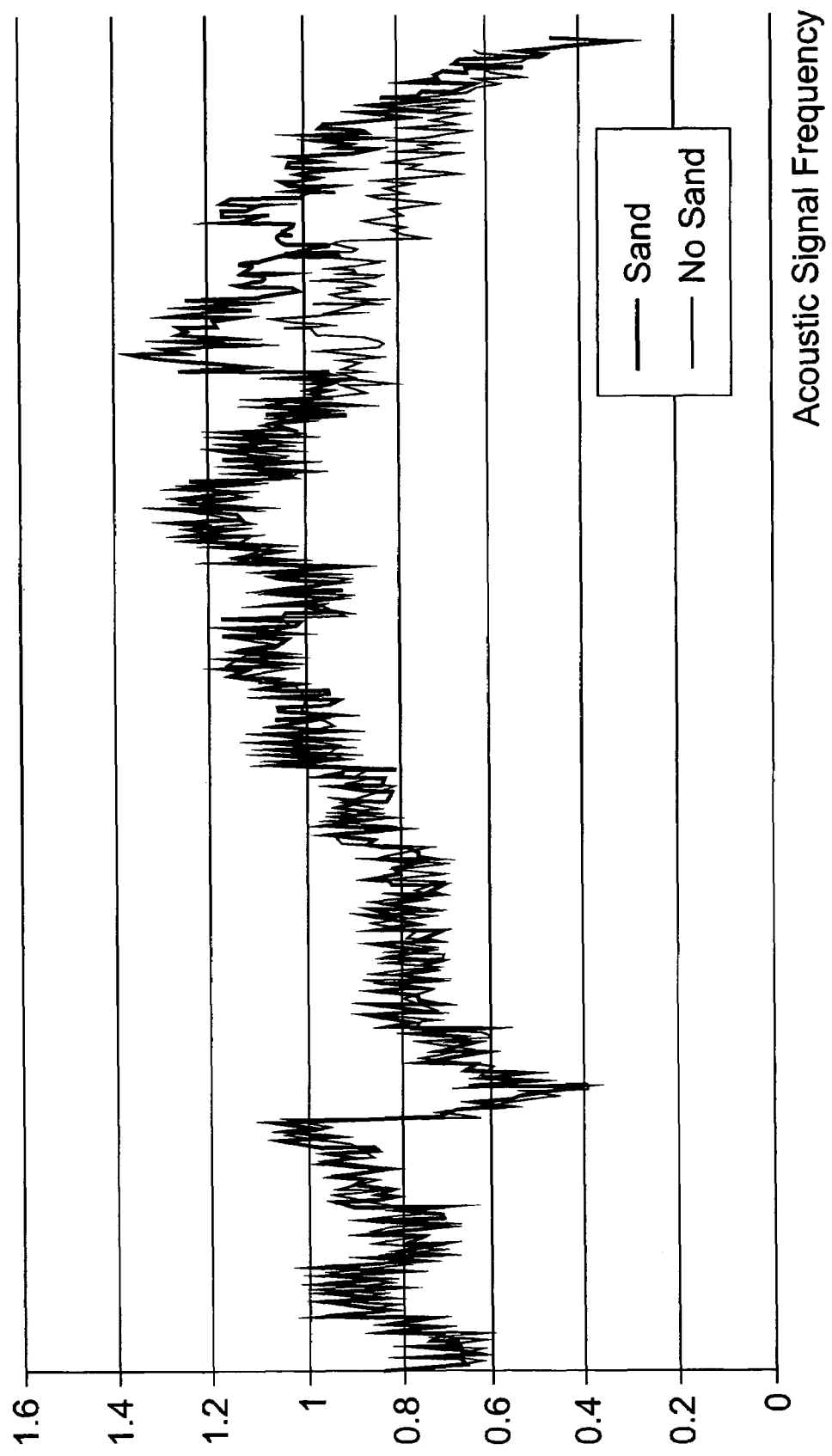
FIG. 1 is a downhole frequency spectrum showing conditions under normal production and with sand production in accordance with a first and second aspect of the present invention.

FIG. 1 illustrates the signals received from such a deployed optical fiber 10 when the acoustic frequency is measured and analysed at two different points in the well where the dark trace shows the frequency signals received from a first FBG 12 and the lighter colour trace shows the signals received from a second FBG 12, located either above or below the first FBG 12. The traces indicated that the first FBG 12 has "heard" any sand production whilst the second FBG 12 has not "heard" any sand production. This can be seen from the relatively substantial difference in the amplitude of the traces at the Right hand side thereof on FIG. 1.

Embodiment 3

Identification and Location of Localized Events

One or more embodiments in accordance with the third aspect of the present invention will now be described.

An acoustic profile can also be used to identify the presence of flow behind casing 20 or in the annulus between the tubing 16 and the casing 20 because such flow will generate an acoustic signal. When a well is provided with an optical fiber 10 carrying FBGs 12 or is otherwise instrumented as described above is shut in (not flowing), or is flowing at a low rate, or when a measurement is compared to a baseline reference survey, acoustic events detected across a particular section, but not across the rest of the instrumented section, are indicative of localised events.

Acoustic activity when the well is shut in is an indication of possible flow behind the tubing, or from tubing 16 to annulus (or vice versa).

Similarly, a leak in the tubing 16 will generate noise. A leak may not be easily detectable on a thermal profile if it is too small to generate significant thermal effects, whereas the acoustic frequency characteristics of such a leak may be quite distinctive. The acoustic profile can thus be used to identify and locate tubing 16 leaks.

Similarly, cross-flow from one zone to another will generate flow noise. When the well is shut in, flow noise between two or more zones is indicative of cross-flow. The acoustic profile can thus be used to identify and locate cross-flow between zones.

Embodiment 4

Determining Apparent Flow Velocity from an Event

Embodiments in accordance with the fourth aspect of the present invention will now be described.

Determining Apparent Flow Velocity from Naturally Occurring Thermal Events

An important application of temperature measurements across the reservoir is the allocation of flow to particular zones. Whilst a correlation exists between the temperature profile and flow from a particular zone, this relationship depends on a number of variables and is notoriously difficult to quantify. A fluid velocity measurement would significantly improve the reliability and accuracy of flow allocation calculations.

A feature of FBGs 12, particularly in comparison to other downhole fiber techniques such as Raman Distributed Temperature Sensing (DTS), is the ability of high sampling rates. Typically, a Raman DTS system will require from 2-30 minutes to make a measurement. An FBG 12 can be read at a rate of up to several kHz.

Any instability in the flow, i.e. turbulent flow, solids production, slugs or surges, etc., will generate a short term event that cannot normally be detected by the long time-constant Raman DTS measurement. A high sample-rate FBG sensor, however, can detect relatively high-frequency events or transients.

While thermal events can be detected, the thermal lag (created by the time required for heat to be transferred through multiple layers of tubing in conjunction with the heat sink effect of all of the in-well tubulars) limits the detection of such events through purely thermal analysis. An acoustic or mechanical event, however, will be detectable over much shorter time-scales. At any given point, an FBG acoustic sensor 12, for example, will be able to produce a measurement of the level of noise across the measured frequency spectrum. The same measurement can be repeated at a second FBG sensor 12 a little further up the well. Further measurements can be made at subsequent sensors 12 further up the well.

Standard and well-known cross-correlation techniques can be used to calculate when an event passing one sensor reaches a subsequent sensor 12. Knowing the distance between the two sensors 12, this measured "time of flight" of the event can be used to calculate the apparent flow velocity.

Figure 2:
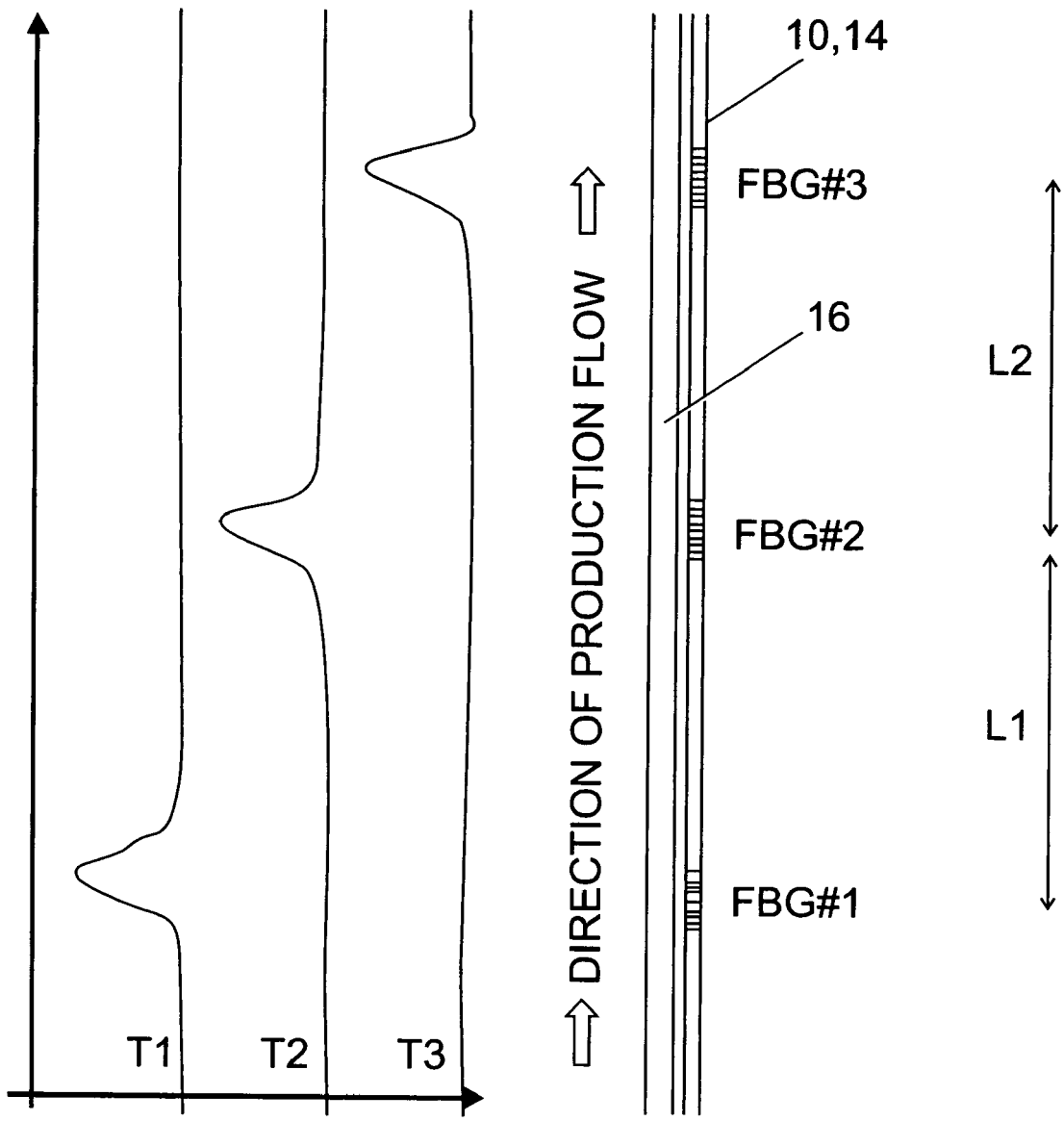
FIG. 2 is a schematic diagram showing a production tubing alongside an optical fiber provided with FBG sensors deployed within a protective tube and also shows a diagram illustrating the movement of an event in time passed three FBG sensors.

FIG. 2 shows an event passing three FBG sensors 12 in a system. At time T1, the event is carried by production flow past FBG #1. At time T2, the event passes FBG #2 and at time T3, it passes FBG #3. Distances L1 (between FBG #1 and FBG #2) and L2 (between FBG #2 and FBG #3) are defined at the time of manufacture and are therefore known.

Cross-correlation of trace T1 against T2 will determine the time required for the event to travel from FBG #1 to FBG #2. Similarly, the time taken for the event to travel from FBG #2 to FBG #3 can be determined.

From here, a simple [speed=distance/time] calculation will provide the apparent flow velocity.

While there are a number of potential sources of error or uncertainty in individual correlations, these can be overcome by performing multiple or continuous correlations, and stacking (or otherwise averaging) them to remove statistical anomalies. Accuracy, speed of calculation and minimisation of anomalous results can also be improved by limiting the correlation step and interval parameters to approximate expected values of apparent flow velocities.

Determining Apparent Flow Velocity from Induced Thermal Events

When a fiber package 10 is deployed such that the check valve releases into the production bore, as is the case when injected into an existing chemical injection line, a thermal event can be induced in the production bore by injecting fluid past the micro-tube, through the injection line and check valve, into the production bore. This can be seen in FIG. 3.

Such injected fluid will normally be at a different temperature than the produced fluid. The resultant thermal event can be observed as it flows with the produced fluid up the production bore. Even where the injected fluid has become warmed up through proximity to the production fluid, it will still be colder (or hotter, if heated fluid is used) than the production fluid.

To generate faster thermal transients, fluid can be injected until a steady state is achieved. At this point, the thermal event may be pulsed, i.e. the injection is stopped and re-started, ensuring the greatest possible temperature differential between injected and produced fluids, and thus generating a distinctive and characteristic transient event that can be detected easily.

Liquid or gas can be injected, as appropriate to be compatible with the fluid being produced. The thermal event may be a "Hot Event" such as the injection of steam or a "Cold Event" such as a cold fluid from surface. Alternatively, thermal events can be induced from surface by changing flow rates, for example, by altering the choke position.

Figure 3:
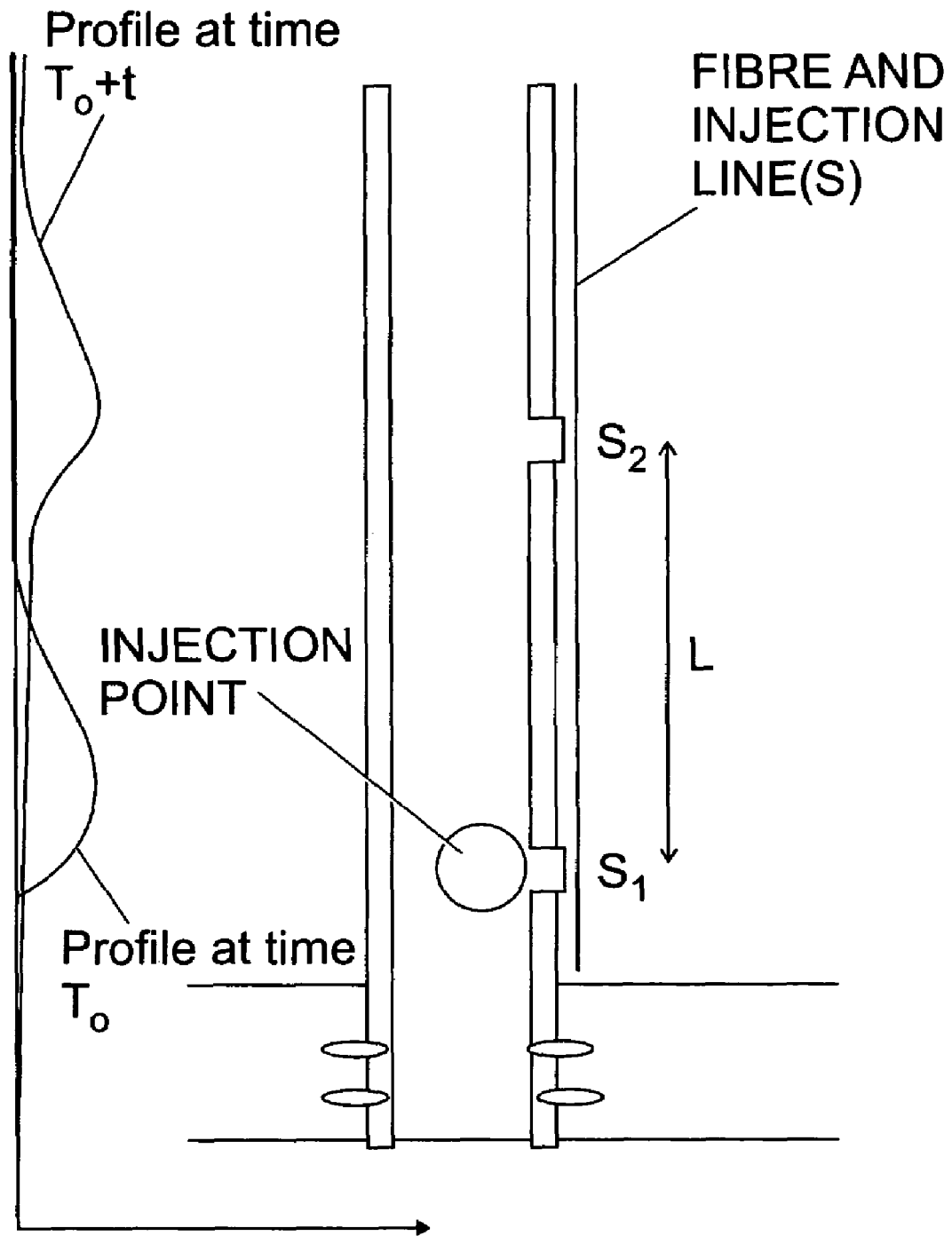
FIG. 3 is a schematic diagram showing a production tubing alongside an optical fiber provided with FBG sensors deployed within a protective tube and also shows a diagram illustrating the movement of an induced thermal event in time.

It can be seen from FIG. 3 that, when a thermal event is induced in the flow, the time "t" taken for this event to pass between two points S1 and S2 can be obtained from cross-correlating the signal at these points.

Provided the distance between the two points is known, Apparent Flow Velocity "V" is simply:

$$V = \frac{L}{t}$$

Determining Apparent Flow Velocity from Induced Acoustic Events

A limitation of the previous situation described (Determining Apparent Flow Velocity from induced thermal events) is the thermal lag inherent in temperature changes in the production bore of the production tubing 16 reaching the sensor, which is located on the outside of the production tubing 16.

Knowing the distance "L" between the acoustic generator and two or more sensors, the signal transit time "t" in the production fluid can be measured. The apparent fluid velocity is then derived from the difference between the transit time under flowing and static conditions.

Figure 4:
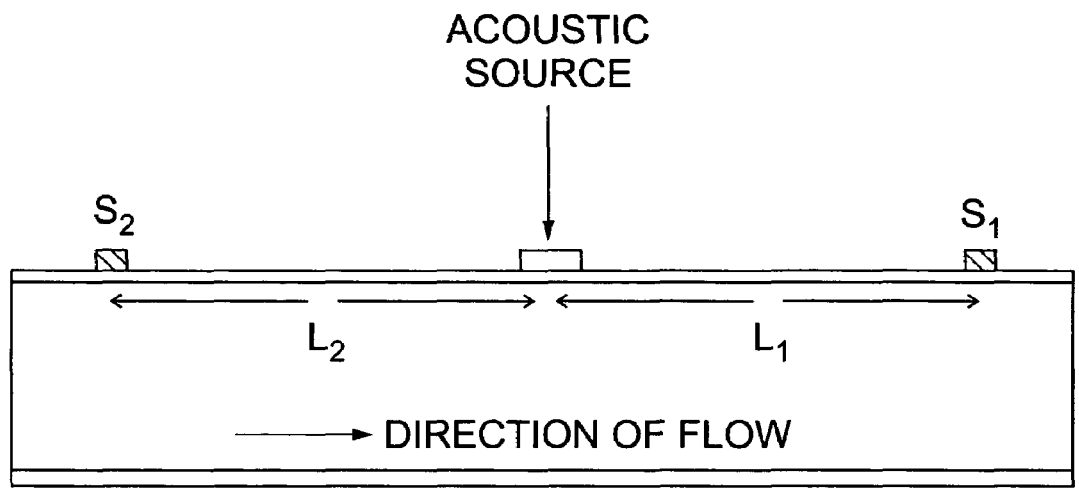
FIG. 4 is a schematic diagram showing a production tubing provided with two acoustic sensors and an acoustic source and also shows a diagram illustrating the trace output by the two sensors versus time for an acoustic event induced by actuation of the acoustic source which can be used to determine the apparent flow velocity of the production fluid.
Figure 4:
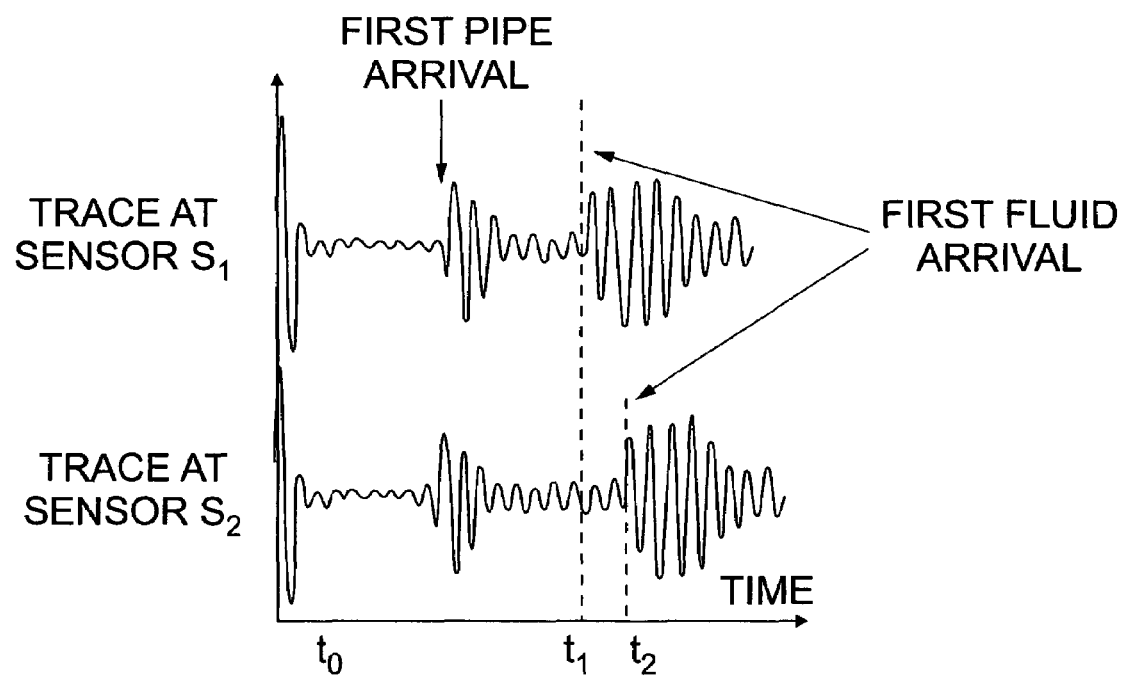

An acoustic source, which is described in more detail below, can be used instead of a thermal source to create an acoustic event that can be measured at two or more sensors 12, and this is shown in FIG. 4.

An enhanced embodiment of the method, as shown in FIG. 4, is to place two sensors 12, one either side of the acoustic source. The difference between the two transit times (i.e. source to upstream sensor and source to downstream sensor) is then directly proportional to the apparent flow velocity.

For example, when coupled with an electrical conductor (such as a TEFAC™ cable available from Wood Group in Houston, Tex., USA), an acoustic or ultrasonic source such as Piezo Technologies' ETALON™ range of downhole transducers or alternatively, a mechanical source can be used, similar to those used for electric wireline acoustic logs.

FIG. 4 illustrates an induced acoustic event where:
L1=distance from acoustic source to acoustic sensor S1 (m)
L2=distance from acoustic source to acoustic sensor S2 (m)
t1=time for acoustic signal to reach S1 (s)
t2=time for acoustic signal to reach S2 (s)
Va=propagation velocity of acoustic signal in stationary medium (ms−1)
Vf=velocity of medium (ms−1)
Vs=velocity of signal (ms−1)

For propagation in the direction of flow, $$Vs=(Va+Vf)=L1/t1 \qquad (1)$$

For propagation in the direction opposite to flow, $$Vs=(Va-Vf)=L2/t2 \qquad (2)$$

Rearranging (2) gives, $$Va=L2/t2+Vf \qquad (3)$$

Substituting (3) into (1) to eliminate Va gives, $$Vf=\tfrac{1}{2}(L1/t1-L2/t2)$$

where: L1 and L2 are constants, t1 and t2 are measured variables.

The limitations of this application are likely to be related to the distance a signal can travel and still be detectable, particularly in areas of good cement bond quality, where acoustic signals are attenuated significantly.

Apparent Flow Velocity from Induced Pressure Events

Figure 5:
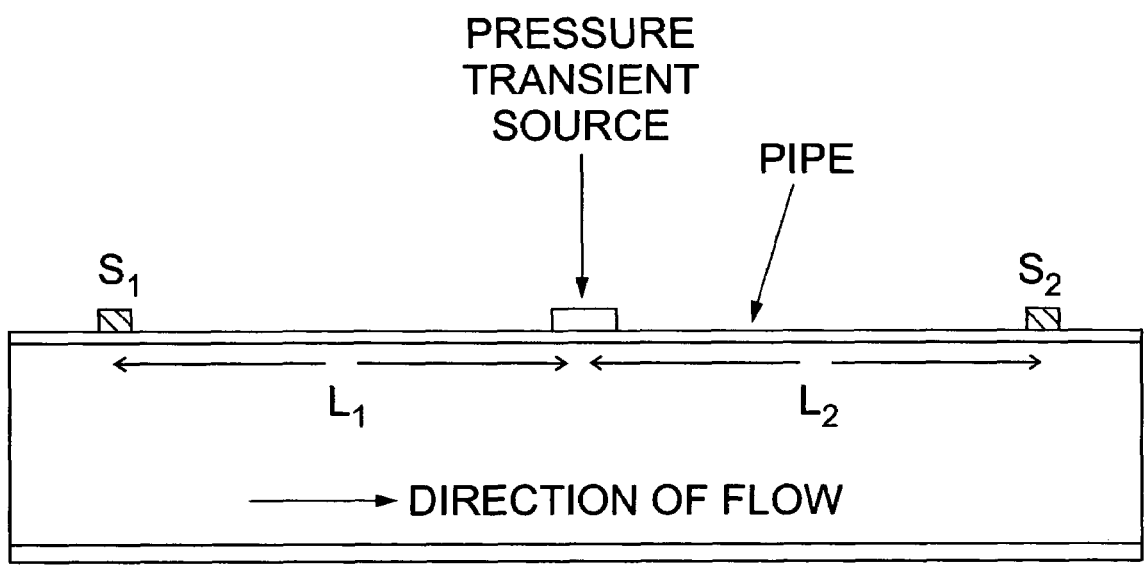
FIG. 5 is a schematic diagram showing a production tubing provided with two pressure sensors and a pressure transient source.

The previous situation described (Determining Apparent Flow Velocity from induced acoustic events) the use of an acoustic signal to determine apparent flow velocity.

Where two pressure sensors are used in place of the acoustic sensors, the same principles can be used to determine the transit time of an induced pressure event, and this is shown in FIG. 5. A suitable pressure sensor is a ROC-D™ downhole gauge (product no. 9385-6010) available from Wood Group of Houston, Tex., USA.

A means, such as the pressure transient source shown in FIG. 5, is required to generate such a pressure event. One such means is to inject liquid or gas into the well between two pressure sensors.

Alternatively, a sharper transient may be achieved by interrupting the flow of such an injected liquid or gas. Alternatively, a mechanical chamber (not shown) or electrical solenoid (not shown) can be suddenly released to create a local pressure transient.

In this example, issues of pipe arrival need not be considered, as the only signal path between the pressure transient source and the pressure sensor is through the production fluid.

Embodiment 5

Active Downhole Strain Monitoring

One or more embodiments in accordance with the fifth aspect of the present invention will now be described.

Figure 6:
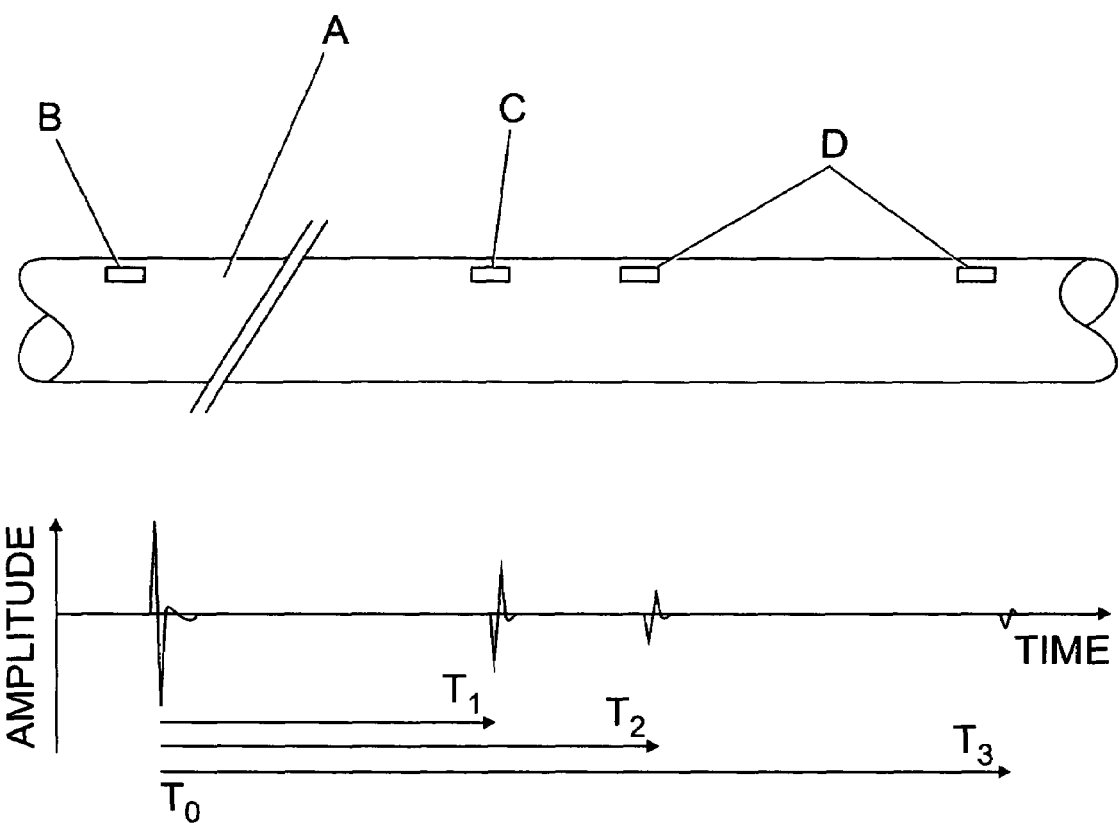
FIG. 6 is a schematic diagram of a configuration of an acoustic transmitter and one or more acoustic receivers mounted on a casing string for monitoring the acoustic strain in the casing string and also shows a diagram illustrating the trace output by the three illustrated receivers.

A receiver or optionally two or more receivers, which may be acoustic, displacement or may use some other principle, are mounted on the casing string (A.) in an oil, gas or water well and this is shown in FIG. 6. It is preferred however that the two or more receivers are preferably FBGs 12 as shown in FIG. 7. A relevant signal is generated some distance away, possibly at surface, or on the seabed (which is more likely in the case of a subsea well), or at one or more locations in the well and the latter example is shown in FIG. 6 by transmitter (B.) being attached to the outer surface of the casing string (A.).

The distance travelled by the signal generated (which in the case of FIG. 6 is generated by transmitter B.) is a function of the speed of the signal travelling along the sidewall of the casing string (A.) and the physical length of the signal path, i.e. the distance between the transmitter (B.) and the one (C.) or more (D.) receivers.

The speed of the signal between generation at the transmitter (B.) and arrival at the receiver (C.) is a well known quantity.

The distance travelled by the signal can then be calculated by measuring accurately the transit time from transmitter to receiver.

When the casing string (A.) is under tension, the distance travelled by the signal from transmitter (B.) to receiver (C.; D.) will increase, which will result in an increase in measured transit time. Similarly, under compression, the measured transit time will decrease.

The limitations of this application are likely to be related to the distance a signal can travel and still be detectable, particularly in areas of good cement bond quality, where acoustic signals are attenuated significantly.

If the casing (A.) is buckled, however, the signal path may be longer than the physical length of the casing (A.), particularly in the case of helical or (to a lesser extent) Euler buckling, leading to under-estimation of the severity of any measured deformation.

A further limitation of this method is introduced by any deformation of downhole tubulars (A.). If the casing (A.) that forms the acoustic signal path is buckled, the signal path may be longer than the physical length of the casing (A.), particularly in the case of helical or (to a lesser extent) Euler buckling, leading to under-estimation of the severity of any measured deformation. In this case, an absolute measurement may be misleading, and it becomes important that a measurement is seen in the context of preceding measurements as any such deformation develops.

Effects of stress on propagation speed such as stress in the metal forming the acoustic signal path will affect the propagation speed of an acoustic (or other) signal. Such effects must be modelled and taken into account in calculating any displacement from propagation speed measurements.

Advantages of this example include:

The receivers (C.; D.) are mounted only at specific measurement points on the casing (A.), for example on a cable protector at a casing joint. This renders the measurement independent of tension in the instrument cable, which in the case of the receivers being FBGs, is the optical fiber 10.

Point sensors such as receivers (C.; D.) make absolute measurements whereas continuous sensors (such as distributed strain fibers such as FBGs) will be affected by strain in the vicinity of the measurement point of interest.

The proposed method can be implemented using fiber optic FBG sensors, or alternatively using the downhole infrastructure of an electronic monitoring system (such as the ROC™ system available from Wood Group of Houston, Tex., USA) as a basis for power and communications, or the Sodesep Radial Bond Tool (RBT) downhole acoustic electronic detection circuitry which is also available from Wood Group of Houston, Tex., USA, although it should be noted that other suitably modified systems from other manufacturers could also be used.

Embodiment 6

Passive Downhole Strain Monitoring

One or more embodiments in accordance with the sixth aspect of the present invention will now be described.

Stress waves in metals are generated by events such as impact, fatigue cracking, or abrasion. The duration of stress wave emissions is only several microseconds to a few milliseconds. Such transient events propagate away from the initiation site as shear and compression waves at the speed of sound in metal. The shear waves introduce deflections on the surface of the metal which will excite an absolute motion sensor such as an accelerometer or an acoustic sensor.

When a receiver is used which is capable of detecting acoustic or vibrational signals, events in the frequency range of such stress wave emissions can be detected and differentiated from background noise. It should be noted that a series of suitable receivers/sensors, which are preferably a series of FBGs 12 as shown in FIG. 7, are located within the casing string 20 as before but would likely be placed in order to optimise the detection of displacement due to strain. The accumulation and distribution with time of such signals received by the sensors/FBGs 12 within an individual well or across a field will enable correlations of events to be made. Such a correlation will contain information as to the direction and magnitude of acoustic or vibrational events including, but not limited to, compression, tension or bending of the casing 20, or similar occurrences within the formation rock surrounding the casing 20.

Many of the advantages described in the previous embodiments will also hold for this embodiment 6.

The acoustic profile hereinbefore described using the sensors (which are preferably FBGs 12) fixed in position with respect to the production tubing 16 can be virtually simultaneous across the length of the measured section, thus eliminating misinterpretations due to acoustic signal changing with time, which is a disadvantage experienced by conventional "noise log" operations since such a conventional operation may misinterpret, for example, an event that is detectable over a significant length of the zone of interest, but which is not present and consistent as the sensor moves across the zone of interest.

Modifications and improvements may be made to the embodiments hereinbefore described without departing from the scope of the invention. For instance, while the use of optical fiber 10 as hereinbefore described provides advantages in terms of high levels of bandwidth and data communication rate, many of the embodiments hereinbefore described can function equally well using electronic or hybrid systems rather than optical fiber 10 alone. In other words, an electronic or hybrid system could be used instead of or in conjunction with the optical fiber 10 and FBGs 12 to achieve the various monitoring applications described.

Furthermore, other signal types are also considered as alternatives for many of the embodiments hereinbefore described. Electromagnetic pulses are possible, for example, in place of some acoustic signals.

Furthermore, pressure pulses over a known distance through the annulus between the production tubing and casing string may be used to determine the absolute distance from a pressure transmitter to a pressure sensor/receiver by measuring the transit time (by using the same principle as acoustic transmission); in other words, a pressure transmitter and receiver would replace the acoustic transmitter/receiver 12 hereinbefore described, although this will be limited by packers and other pressure retaining devices.

I claim:

1. A method of determining and/or identifying a flow regime of fluid in a well, the method comprising the steps of:

providing an optical fiber having a plurality of spaced apart fiber Bragg gratings formed thereon, with elongated portions of the optical fiber being disposed between adjacent ones of the fiber Bragg gratings;

positioning the optical fiber adjacent a tubular string in the well;

monitoring signals received from two or more of the fiber Bragg gratings;

measuring an acoustic signal at each portion of the optical fiber between the fiber Bragg gratings over time to produce an acoustic profile; and analyzing frequencies of said acoustic profile to determine the flow regime.

2. The method of claim 1, wherein the acoustic signal that is measured is an interferometric signal of a respective portion of the optical fiber between corresponding adjacent fiber Bragg gratings.

3. The method of claim 1, further comprising the step of comparing the determined flow regime to a reference flow regime.

* * * * *